United States Patent [19]

Ibata et al.

[11] Patent Number: 4,668,820

[45] Date of Patent: May 26, 1987

[54] METHOD OF PREPARING POLYPRENYL COMPOUNDS OR MIXTURES THEREOF

[75] Inventors: Koichi Ibata; Tetsuo Takigawa; Masafumi Okada; Masao Mizuno; Takashi Nishida, all of Kurashiki, Japan

[73] Assignee: Kuraray Co., Ltd., Kurashiki City, Japan

[21] Appl. No.: 722,173

[22] Filed: Apr. 10, 1985

Related U.S. Application Data

[63] Continuation of Ser. No. 494,876, May 16, 1983, abandoned.

[30] Foreign Application Priority Data

May 17, 1982 [JP] Japan .................. 57-83656

[51] Int. Cl.$^4$ .................. C07C 67/48; C07C 69/025; C07C 33/02; C07C 67/52
[52] U.S. Cl. .................. 560/248; 560/249; 568/875
[58] Field of Search .................. 568/875; 560/248, 249

[56] References Cited

U.S. PATENT DOCUMENTS 3,526,669  9/1970  Fukawa et al. .................. 568/875
3,549,668 12/1970  Fukawa et al. .................. 568/875
4,013,731  3/1977  Asahina et al. .................. 568/875

FOREIGN PATENT DOCUMENTS 0054753  6/1982  European Pat. Off. ............ 568/875

OTHER PUBLICATIONS

Chemical Abstracts, vol. 82, abstract 95727v, Hannus et al., "Polyisoprenols in *Pinus sylvestris* Needles".
Zinkel et al., "Phytochemistry", (1972), vol. 11, pp. 3387-3389.
Zinkel et al., "Phytochemistry", (1972), vol. 11, pp. 425-426.
Chemical Abstracts, vol. 71, abstract no. 88431r, Tomita et al., "Terpenoids, XXII, Chemotaxonomy of the Cupressaceae, 1, The Composition of the Essential Oil from the Wood of *Thuja koraiensis*".
Chemical Abstracts, vol. 87, abstract 114628n, Caputo et al., "Diterpenoids of Araucariaceae, VII, Minor Diterpenes from the Resin of *Araucaria imbricata*".
Journal of the Chemical Society Perkin I, No. 10, 1980, London, Suga et al., "Structure and Biosynthesis of Cleomeprenols from the Leaves of *Cleome spinosa*".
Tetrahedron Letters, vol. 50, 1978, London, Horii et al., "Ulmoprenol, A New Type $C_{30}$—Polyprenoid From Eucommia Ulmoides, Oliver".
Patent Abstracts of Japan, vol. 6, No. 177, Sep. 11, 1982.

*Primary Examiner*—J. E. Evans
*Attorney, Agent, or Firm*—Burns, Doane, Swecker & Mathis

[57] ABSTRACT

Polyprenols or esters thereof, which are similar in the trans and cis configurations to dolichol, or mixtures thereof are obtained from the leaves of plants belonging to the genus Pinus L. of the family Pinaceae by extraction, if necessary followed by hydrolysis, esterification or transesterification or a combination thereof. These polyprenyl compounds and mixtures thereof are useful as favorable starting materials for the synthesis of dolichol.

6 Claims, No Drawings

1

METHOD OF PREPARING POLYPRENYL COMPOUNDS OR MIXTURES THEREOF

This application is a continuation of Ser. No. 494,876 filed 05/16/83, now abandoned.

BACKGROUND OF THE INVENTION

1. Field of the Invention

This invention relates to a method of preparing polyprenyl compounds or mixtures thereof. More particularly, the invention relates to a method of preparing polyprenols or esters thereof, or mixtures thereof, which have trans and cis configurations similar to those of dolichol and are useful as advantageous starting materials for the synthesis of dolichol.

2. Description of the Prior Art

Dolichol was first isolated in 1960 from the human kidney and such animal organs as ox kidney, pig kidney, pig heart, pig liver and rat liver by J. F. Pennock et al [see *Nature* (London), 186, 470 (1960)]. Later, it was elucidated that dolichol is a mixture of polyprenol homologs having the general formula:

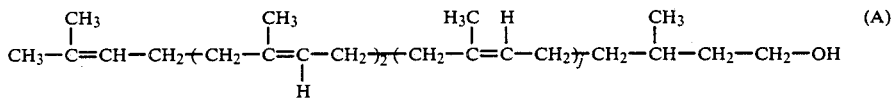

wherein

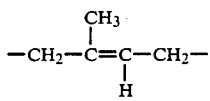

represents a trans-isoprene unit, and

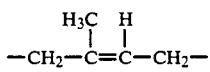

represents a cis-isoprene unit (the same definitions being consistently applied throughout the present text), and the number j of cis-isoprene units in the above formula is generally distributed between 12 to 18 and the three homologs in which j is 14, 15 and 16 are present in major proportions [R. W. Keenan et al., *Biochemical Journal*, 165, 405 (1977)]. It is also known that dolichol is widely distributed in mammals, and performs a very important function in sustaining the lives of organisms.

For example, J. B. Harford et al. demonstrated by in vitro tests using the calf or pig brain white matter that exogenous dolichol enhances incorporation of carbohydrates such as mannose into lipid, and consequently increases the formation of glycoproteins which are important for maintaining the lives of organisms [*Biochemical and Biophysical Research Communications*, 76, 1036 (1977)]. Since the effect of dolichol to incorporate carbohydrates into lipid is remarkable in mature animals as compared with those in the actively growing stage, the action of dolichol has attracted attention for its possible retarding or prevention of aging.

R. W. Keenan et al. state that it is important for organisms which rapidly keep growing, for example, those in the infant stage, to take dolichol extraneously such as to supplement the dolichol produced by biosynthesis within their own body [*Archives of Biochemistry and Biophysics*, 179, 634 (1977)].

Akamatsu et al. determined the quantity of dolichol phosphate in the regenerated liver of a rat and found that the quantity determined is much smaller than that in normal liver and the function of the liver tissues to synthesize glycoproteins is drastically reduced and that the addition of exogenous dolichol phosphate improves the reduced function of glycoprotein synthesis (reported at the 1981 Conference of the Japanese Society of Biochemistry).

Thus, dolichol is a very important substance for living organisms, and it is strongly desired to develop its use as a medicine or an intermediate for the production of medicines, cosmetics, etc.

However, since dolichol has hitherto been difficult to obtain, sufficient research works have been impossible. For example, only about 0.6 g at most of dolichol can be obtained from 10 kg of pig liver through complicated separating procedures [see J. Burgos et al., *Biochemical Journal*, 88, 470 (1963)].

On the other hand, it is extremely difficult by present day techniques of organic synthesis to produce dolichol by a wholly synthetic process, as can be seen in the light of the complex and unique molecular structure thereof.

It is to date known that polyprenol compounds can be extracted from various plants, and so far, following polyprenols have been successfully extracted.

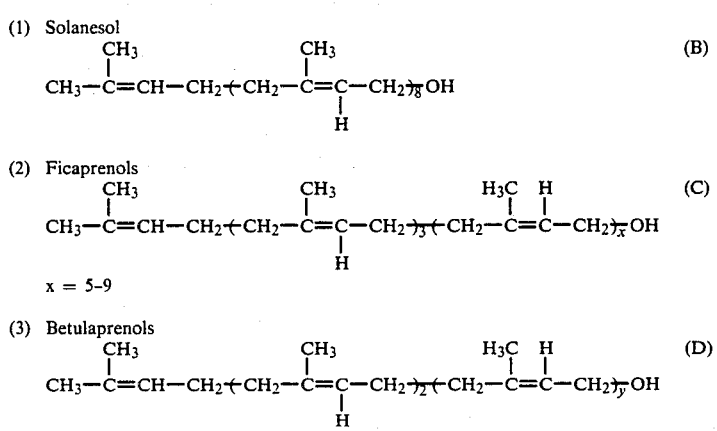

y = 4-6

Betulaprenols have a structure similar to dolichols in that a group of two trans-isoprene units is connected to the omega-terminal isoprene unit and then a group of cis-isoprene units follows. However, the betulaprenols so far known contain up to six cis-isoprene units at most, and in order to synthesize dolichols containing homologs having 14, 15 and 16 cis-isoprene units respectively as major components from these betulaprenols, it is necessary to link at least 8 isoprene units while maintaining them in cis-form. This procedure is almost impossible by the present-day organic synthetic techniques.

K. Hannus et al. reported that a polyisoprenyl fraction in an amount of about 1% dry weight was isolated from the needles of *Pinus sylvestris* and the fraction consisted of polyisoprenyl acetates with 10 to 19 isoprene units predominantly in the cis-configuration [*Phytochemistry*, 13, 2563 (1974)]. However, their report does not explain the details of the trans and cis configurations in said polyprenyl acetates. Furthermore, according to a report of D. F. Zinkel et al., a $C_{90}$ polyprenol containing 18 isoprene units or a homologous series of polyprenols averaging 18 isoprene units is present in *Pinus strobus* needle extracts [cf. *Phytochemistry*, 11, 3387 (1972)]. However, this report does not contain any detailed analysis of the trans and cis configurations in said polyprenol.

Some of the present inventors, together with their colleagues, previously found that extraction of the leaves of *Ginkgo biloba* and *Cedrus deodara* followed by an adequate separation procedure, such as chromatography or fractional dissolution, if necessary following hydrolysis, gives a polyprenyl fraction composed of a mixture of polyprenols and/or acetates thereof which contain 14–22 isoprene units in quite the same trans/cis configurations as in mammalian dolichols and that said polyprenyl fraction is very similar in the chain length distribution of polyprenyl homologs to mammalian dolichols, the only difference being the absence in said fraction of the alpha-terminal saturated isoprene unit and that said polyprenyl fraction, if desired, can be separated relatively easily into the individual constituent polyprenyl homologs (each being homogeneous with respect to the number of isoprene units), and proposed a method of producing dolichols or precursors thereof which comprises reacting such polyprenyl compound or fraction or a reactive derivative thereof with a Grignard reagent or lithium compound derived from a 4-hydroxy-2-methylbutyl halide or a functional precursor thereof (EP No. 0 054 753 A1 published on June 30, 1982; U.S. patent application Ser. No. 371,487 which is a continuation-in-part of U.S. patent application Ser. No. 324,636, filed Nov. 24, 1981, now abandoned).

However, the extraction of the above-mentioned polyprenyl fraction from the leaves of *Ginkgo biloba* and *Cedrus deodara* is limited regionally as well as quantitatively from the natural resource viewpoint.

Accordingly, an object of the invention is to provide a method of obtaining polyprenyl compounds or mixtures thereof, which are usable as advantageous starting materials in the synthesis of dolichol, from plants other than the above-mentioned *Ginkgo biloba* and *Cedrus deodara*.

Other objects of the invention will become apparent from the following detailed description.

SUMMARY OF THE INVENTION

Surprisingly, it has now been found that the polyprenyl compounds contained in polyprenyl fractions (polyprenyl compositions) extracted from the leaves of plants belonging to the genus Pinus L. of the family Pinaceae are very similar in structure to mammalian dolichols and therefore very suited for use as intermediates in the synthesis of mammalian dolichols. More specifically, said polyprenyl fractions each is a mixture of polyprenols and/or acetates thereof, in which, like in dolichols, a group of two trans-isoprene units followed by a group of 10 to 18 cis-isoprene units is linked to the omega-terminal isoprene unit. With regard to the number of cis-isoprene units, those four homologs in which said number is 12, 13, 14 and 15 are predominant. Therefore, said polyprenols are very close to mammalian dolichols except that they have no alpha-terminal saturated isoprene unit and that the average number of cis-isoprene units for said fraction is smaller by 1 to 2.

Thus, the present invention provides a method of preparing polyprenyl compounds or mixtures thereof represented by the general formula

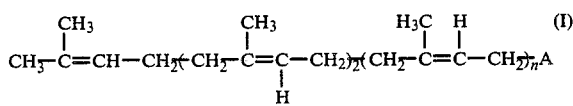

wherein

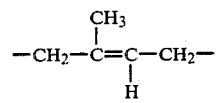

represents a trans-isoprene unit,

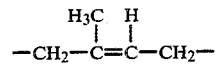

represents a cis-isoprene unit, n is an integer of 10 to 18, and A represents a hydroxyl group or an acyloxy group, which comprises extracting leaves, or needles, of a plant belonging to the genus Pinus L. of the family Pinaceae with an organic solvent and isolating a polyprenyl compound or a mixture of polyprenyl compounds from the extract, if necessary following or followed by subjecting the extract or the isolated compound or mixture to one or more reactions selected from among hydrolysis, esterification and transesterification.

DETAILED DESCRIPTION OF THE INVENTION

The plants belonging to the genus Pinus L. of the family Pinaceae, which are used as the starting material, are the plants belonging to the order Coniferales of the class Coniferopsida of the subdivision Gymnospermae of the division Spermatophyta and includes, among others, *Pinus densiflora*, *Pinus thunbergii*, *Pinus sylvestris*,

*Pinus strobus, Pinus elliatii, Pinus serotina, Pinus contorta, Pinus ponderosa, Pinus pinea, Pinus taeda, Pinus palustris, Pinus taiwanensis, Pinus rigida, Pinus pinaster, Pinus parviflora, Pinus monticola, Pinus lambertiana, Pinus bungeana, Pinus krempfii, Pinus pumila, Pinus nigra, Pinus clausa* and *Pinus excelsa*, which are preferable from the natural resource viewpoint.

Pine needles to be treated according to this invention may be used undried or after drying. Generally, dried needles are preferred. The degree of drying of the needles should advantageously correspond to a water content, based on the weight of the dried needles, of less than about 30%, preferably less than about 10%. Preferably, the needles are extracted after crushing. This increases the area of contact with the extracting solvent, and results in an increased efficiency of extraction.

The polyprenyl homologs of formula (I) are contained in the pine needles in fairly high concentrations generally in the form of free alcohol and/or acetic acid ester. In order to extract the polyprenyl homologs from the needles effectively, the use of oil-soluble organic solvents capable of well dissolving the polyprenyl homologs is convenient.

Suitable oil-soluble organic solvents that can be used in practicing this invention have a dielectric constant ($\epsilon$) of not more than 32.7, preferably not more than 25.0, more preferably not more than 20.7. Specifically, solvents such as exemplified below are used either singly or as a mixture of two or more.

(a) Hydrocarbons such as petroleum ether, pentane, hexane, heptane, benzene, toluene and xylene.
(b) Halogenated hydrocarbons such as chloroform, methylene chloride, carbon tetrachloride, tetrachloroethane, perchloroethylene and trichloroethylene.
(c) Esters such as methyl acetate, ethyl acetate and ethyl propionate.
(d) Ethers such as diethyl ether, diisopropyl ether, tetrahydrofuran and dioxane.
(e) Ketones such as acetone, methyl ethyl ketone, diethyl ketone and diisopropyl ketone.
(f) Alcohols such as methyl alcohol, ethyl alcohol, propyl alcohol and butyl alcohol.

The solvent should desirably be capable of extracting the desired polyprenyl compounds of formula (I) selectively with a high efficiency, while permitting minimization of extraction of other substances. From this standpoint, the hydrocarbons, halogenated hydrocarbons, esters, and ethers having low polarity such as diethyl ether and diisopropyl ether, and ketones are especially suitable among the above-exemplified solvents.

The amount of the extracting solvent is not critical, and can be varied widely depending upon the type of the solvent, the type or condition of the leaves to be extracted, etc. Generally, it is advantageous that the solvent is used in an amount of about 1 to about 100 parts by weight, preferably 5 to 50 parts by weight, more preferably 10 to 30 parts by weight, per part (based on the dry weight) of the pine needles.

The extraction can be carried out by dipping the leaves in the solvent, and if required, stirring the mixture continuously or intermittently. The temperature during the extraction is not critical, but can be varied widely depending upon the extraction conditions such as the type or amount of the solvent used. Generally, the extraction temperature is from about 0° C. to the refluxing temperature of the solvent. Usually, room temperature suffices. Under these conditions, the extraction should advantageously be carried out for a period of 1 to 10 days.

After the extracting treatment, the leaves and other solid components are removed from the dipping solution and if required, the solvent is removed to give a concentrate. The extract is subjected to a separating step consisting of one or more of chromatography, fractional dissolution, fractional refrigerating precipitation and molecular distillation, whereby the desired polyprenyl fraction is recovered.

In the separating step, the formation of the fraction of polyprenyl compounds can be confirmed by determining whether a spot exists at an Rf value of from 0.18 to 0.25 [when A in formula (I) represents a hydroxyl group] and/or from 0.50 to 0.55 [when A in formula (I) represents an acetyloxy group] in thin layer chromatography which is carried out on a TLC plate of Merck Co. precoated with silica gel $60F_{254}$ to a layer thickness of 0.25 mm with a mixture of n-hexane and ethyl acetate in a volume ratio of 9:1 as a developing solvent (developed 10 cm) under such conditions that solanesyl acetate as a standard substance shows an Rf value of from 0.40 to 0.45 in the thin-layer chromatography. It should be understood that in the following description, the Rf values of thin-layer chromatography denote those which are measured under the aforesaid conditions unless otherwise specified.

The operations of the chromatography, fractional dissolution, fractional refrigerating precipitation and molecular distillation used in the step of separating the aforesaid extract are known per se, and in the present invention, too, these methods can be carried out in accordance with known procedures. For the details of these methods, literature references will be cited in lieu of describing them at length. Only those items which need special care will be described below.

(A) Chromatography

For details, reference may be made to H. Heftman, "Chromatography", Reinhold Publishing Co., New York (1961).

When the amount of the extract is small, thin-layer chromatography or liquid chromatography is suitable. For treatment of a large amount of the extract, column chromatography is suitable.

Examples of suitable chromatographic carriers are silica gel, alumina, Florisil, Celite, activated carbon, and cellulose. Silica gel is especially preferred.

Examples of the developing solvent usable in the separating operation on a silica gel column include hexane/ethyl acetate (volume ratio from 98:2 to 80:20), hexane diisopropyl ether (volume ratio from 95:5 to 80:20), petroleum ether/methyl acetate (volume ratio from 98:2 to 80:20), petroleum ether/isopropyl alcohol (volume ratio from 99:1 to 90:10), benzene/diethyl ether (volume ratio from 95:5 to 80:20), benzene/ethyl acetate (volume ratio from 98:2 to 80:20), and chloroform and methylene chloride.

(B) Fractional dissolution

For details, reference may be made to L. C. Craig, "Technique of Organic Chemistry", Vol. 3, Interscience (1951).

The polyprenyl compounds of formula (I) are easily soluble in non-polar solvents such as pentane and hexane, and are sparingly soluble in polar solvents such as methanol or water. Hence, the polyprenyl compounds of formula (I) can be purified by the fractional dissolving method utilizing differences in solubility in these solvents. For example, a crude product such as a concentrate of the extract is dissolved in the aforesaid nonpolar solvent, and then washed with a polar solvent which is immiscible with the nonpolar solvent, whereby impurities easily soluble in the polar solvent can be drastically removed. Suitable nonpolar solvents for use in this method are, for example, hydrocarbons such as petroleum ether, pentane, hexane, heptane, benzene and toluene and halogenated hydrocarbons such as methylene chloride and chloroform. Suitable polar solvents immiscible with such nonpolar solvents are, for example, water and methanol.

(C) Fractional refrigerating precipitation

For details, reference may be made to E. W. Berg, "Physical and Chemical Methods of Separation", Chapters 14 and 15, McGraw-Hill, New York (1963).

The polyprenyl compounds of formula (I) solidify at about $-10°$ C. or less. Hence, the polyprenyl compounds of formula (I) can be purified by allowing the extract to stand at a temperature of not more than $-10°$ C., preferably $-15°$ to $-30°$ C., to solidify the desired compounds, and removing the impurities which do not solidify at these temperatures by a solid-liquid separating technique. The polyprenyl compounds, however, do not have good crystallinity and become a waxy solid. Accordingly, they are difficult to purify completely by this method alone. Preferably, therefore, this method is used in combination with another purifying method.

(D) Molecular distillation

For details, reference may be made to G. Burrows, "Molecular Distillation", Clarendon Press, Oxford (1960).

Since the compounds of formula (I) have a high molecular weight, they can be separated from low-molecular-weight impurities by the molecular distillation method. For example, the extract is subjected to molecular distillation at 100° to 250° C. under a vacuum of $10^{-3}$ to $10^{-5}$ mmHg to divide it into a low-molecular-weight fraction and a high-molecular-weight fraction. The desired compounds are retained in the high-molecular-weight fraction, and the low-molecular-weight impurities can be removed effectively.

When a sufficiently pure polyprenyl fraction cannot be obtained by any of these separating methods, two or more of these separating methods may be used in combination. For example, there can be used a combination of chromatography and fractional dissolution, a combination of chromatography, fractional refrigerating precipitation and fractional dissolution, a combination of chromatography, fractional refrigerating precipitation, fractional dissolution and molecular distillation, a combination of chromatography, molecular distillation and fractional dissolution, a combination of chromatography and molecular distillation, a combination of molecular distillation and fractional dissolution, and a combination of molecular distillation, fractional dissolution and fractional refrigerating precipitation.

As a result of the separating step, a fraction having an Rf value of from 0.18 to 0.25, and/or from 0.50 to 0.55 in thin-layer chromatography can be isolated and recovered. The fraction having an Rf value of 0.18 to 0.25 consists essentially of a mixture of homologs of formula (I) in which A represents a hydroxyl group, and the fraction having an Rf value of from 0.50 to 0.55 consists essentially of homologs of formula (I) in which A represents an acetyloxy group.

The resulting fraction can be separated into the individual homologs by subjecting it further, for example, to high-performance partition liquid chromatography.

Prior to subjecting the extract to the aforesaid separating operation, the extract may be hydrolyzed as required to convert homologs of formula (I) in which A represents an acetyloxy group into homologs of formula (I) in which A represents a hydroxyl group. Of course, the hydrolysis may also be carried out on a fraction having an Rf value of 0.50 to 0.55 obtained by the separating operation. The hydrolysis can be performed by any usual methods known for the hydrolysis of known fatty acid esters. For example, about 5 to about 50 parts by weight of the extract or the fraction is added to 100 parts by weight of a solution of sodium hydroxide or potassium hydroxide in aqueous methanol or ethanol (the alkali metal hydroxide concentration being preferably about 0.1 to 30% by weight), and the reaction is effected at about 25° to 90° C. for about 0.5 to 5 hours.

Referring to the polyprenyl fraction separated and recovered by the method described hereinabove, the fraction having an Rf value of 0.18 to 0.25 consists essentially of a mixture of polyprenol homologs of formula (I) in which A represents a hydroxyl group, and the fraction having an Rf value of 0.50 to 0.55 consists essentially of a mixture of polyprenyl acetate homologs of formula (I) in which A represents an acetyloxy group. The ratio of the former to the latter in the extract is generally in the range of from about 1:99 to about 9:1. The distribution pattern of the polyprenol or polyprenyl acetate homologs is nearly the same for these fractions. The distribution pattern is nearly constant irrespective of the stage of growth of the leaves used as the raw material, the time of harvesting, the region of growth, etc.

Said fraction contains at least four compounds of general formula (I) wherein n is 12, 13, 14 and 15, respectively, as essential components thereof and in substantial amounts, and the total content of the four compounds amounts to at least 70%, generally not less than 75%, by weight based on said fraction.

Although depending on the kind of the Pinus plant used as the raw material and the isolation conditions, said fraction contains a compound of general formula (I) wherein n is 12 generally in an amount of 5–30 percent by weight, more typically 5–25 percent by weight, a compound of general formula (I) wherein n is 13 generally in an amount of 15–45 percent by weight, more typically 20–40 percent by weight, a compound of general fromula (I) wherein n is 14 generally in an amcunt of 10–50 percent by weight, more typically 15–40 percent by weight, and a compound of general formula (I) wherein n is 15 generally in an amount of 5–30 percent by weight, more typically 5–25 percent by weight, based on said fraction.

As is already mentioned hereinabove, the polyprenyl compositions (fractions) obtained from pine needles by extraction in accordance with the present invention are characterized in that they are very close to mammalian dolichols in the distribution pattern for polyprenyl homologs except for the shift of the pattern of distribution of n in general formula (I) by 1 to 2 to the smaller value side as compared with the pattern of distribution of n in general formula (A). In the following table, a comparison is made between polyprenyl fractions extractable from *Pinus densiflora* or *Pinus thunbergii* and pig dolichol with respect to the distribution of polyprenyl homologs. (Human dolichol shows substantially the same distribution pattern as that for pig dolichol.) The numerical values in the parentheses indicate more typical ranges.

TABLE 1

| Value of n in formula (I) and j in formula (A) | Content (percent by weight) Polyprenyl composition extractable from Pinus densiflora or Pinus thunbergii | Pig liver dolichol |
| --- | --- | --- |
| 10 | 0–5 (0–4) | — |
| 11 | 0–10 (1–5) | 0.43 |
| 12 | 5–20 (7–15) | 0.60 |
| 13 | 20–40 (23–35) | 4.38 |
| 14 | 25–50 (27–45) | 25.59 |
| 15 | 10–25 (11–20) | 46.01 |
| 16 | 1–10 (1–7) | 18.79 |
| 17 | 0–5 (0–3) | 3.41 |
| 18 | 0–5 (0–3) | 0.72 |

The average value of n for the polyprenyl compositions obtained by the method of the invention is generally within the range of 12.75 to 14.25.

As is evident from the polyprenyl homolog distribution patterns shown above in Table 1 and comparison between general formula (I) and general formula (A), the polyprenyl compositions obtained by the method of the invention can be converted to mammalian dolichols by adding one saturated isoprene unit to the alpha-terminal of each polyprenyl compound in said compositions. They can be converted to mammalian dolichols also by adding one cis-isoprene unit followed by one saturated isoprene unit to the alpha-terminal. Thus, the polyprenyl compositions obtainable by the method of the invention are very important substances as the intermediates for the synthesis of mammalian dolichols.

In deriving mammalian dolichols from a polyprenyl composition obtained by the method of the present invention, said composition may be used as it is or, if necessary, each polyprenyl compound which is a constituent of said composition may be isolated therefrom for subjecting it to the necessary reactions. Furthermore, said composition or each isolated polyprenyl compound may be subjected to hydrolysis, esterification or transesterification or a combination of two or more of these reactions depending on whether it is in the form of free alcohol or acetate, for conversion of polyprenols to polyprenyl esters or conversion of polyprenyl acetates to other polyprenyl esters of general formula (I) or to polyprenols.

Examples of the polyprenyl ester of general formula (I) which can be produced by the method of the invention are, when A in general formula (I) is represented by RCOO—, those esters in which R is a hydrogen atom, an alkyl group containing 1 to 18 carbon atoms (e.g. methyl, ethyl, n-propyl, isopropyl, n-butyl, sec-butyl, isobutyl, tert-butyl, n-pentyl, isoamyl, n-hexyl, n-octyl, n-decyl, n-undecyl, n-dodecyl, stearyl), an alkenyl group containing 2 to 18 carbon atoms (e.g. 3-butenyl, 3-pentenyl, 4-pentenyl, geranyl, geranylmethyl, farnesyl, farnesylmethyl), a cycloalkyl group containing 5 to 7 carbon atoms (e.g. cyclopentyl, cyclohexyl, methylcyclohexyl, cycloheptyl), an aryl group containing 6 to 10 carbon atoms (e.g. phenyl, tolyl, xylyl, naphthyl), an aralkyl group containing 7 to 11 carbon atoms (e.g. benzyl, phenethyl, methylbenzyl, dimethylbenzyl, alpha- or beta-naphthylmethyl) or a methyl group substituted by 1 to 3 fluorine or chlorine atoms (e.g. monofluoromethyl, trifluoromethyl, monochloromethyl, dichloromethyl). The esterification or transesterification of a polyprenol or polyprenol mixture represented by general formula (I) for the production of the above-mentioned polyprenyl ester or polyprenyl ester mixture can be conducted in the same manner and under the same conditions as in the per se known esterification or transesterification reactions for the production of esters. Thus, for example, the esterification can be easily attained by mixing a polyprenol or polyprenol mixture represented by general formula (I) with a carboxylic acid as desired, such as formic acid, acetic acid, monofluoroacetic acid, monochloroacetic acid, trifluoroacetic acid, propionic acid, butyric acid, caproic acid, caprylic acid, capric acid, lauric acid, palmitic acid, stearic acid, oleic acid, linolic acid, linoleic acid, farnesylic acid, farnesylacetic acid, benzoic acid, 3,5-dimethylbenzoic acid or 4-ethyl-benzoic acid, or an acid halide or acid anhydride thereof in the presence or absence of an esterification catalyst and of a solvent, if necessary with or followed by heating and/or stirring. In a preferred embodiment, the above polyprenol or polyprenol mixture is dissolved in a solvent such as hexane, benzene, methylene chloride, chloroform or diethyl ether, the acid halide mentioned above is added in an amount of 1 to 5 moles per mole of the polyprenol and the resulting mixture is stirred in the presence of 1 to 5 moles of pyridine per mole of the polyprenol at an adequate temperature in the range of from room temperature to the boiling point of the solvent for 1 to 24 hours.

The transesterification is carried out by reacting a polyprenol or polyprenol mixture represented by general formula (I) with a lower alkyl ester (e.g. methyl ester, ethyl ester) of a carboxylic acid as desired (for instance, one of the carboxylic acids mentioned above) optionally in the presence of a transesterification catalyst. In a preferred embodiment, the above polyprenol or polyprenol mixture and a desired carboxylic acid ester and dissolved in a solvent such as benzene, toluene or xylene, sodium hydride is added in an amount of 0.01 to 0.1 mole per mole of the polyprenol and the resulting mixture is refluxed for a period of 2 hours to 5 days.

The polyprenyl compounds or mixtures thereof represented by general formula (I) as obtained by the method of the invention are easily converted to mammalian dolichols, for example by the following routes:

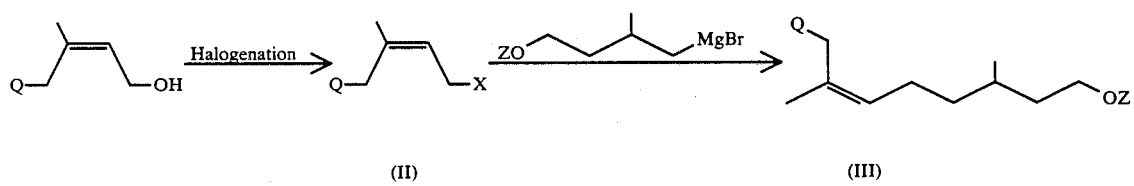

(II)         (III)

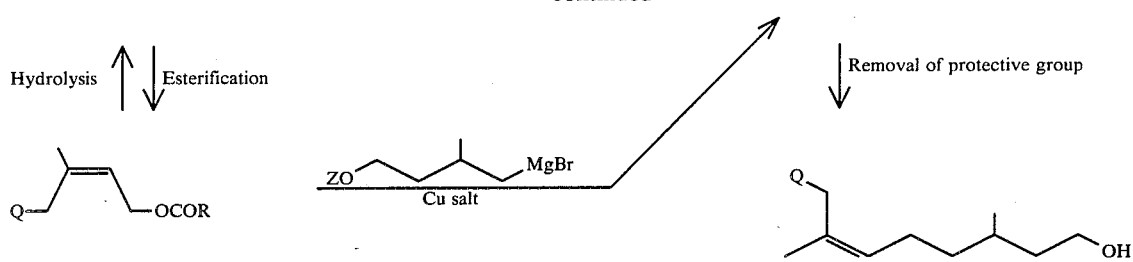

In the above schema, X is a halogen atom, preferably Cl or Br, Z is a hydroxyl-protecting group, such as, for example, tetrahydropyranyl, methoxymethyl or benzyl, OCOR is an acyloxy group and Q is a group of the formula

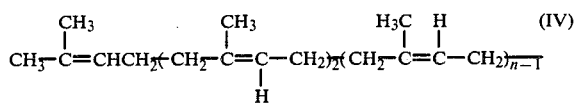

wherein n is as defined for general formula (I).

Dolichol can also be produced by an alternative method recently elaborated by K. Sato et al. illustrated below.

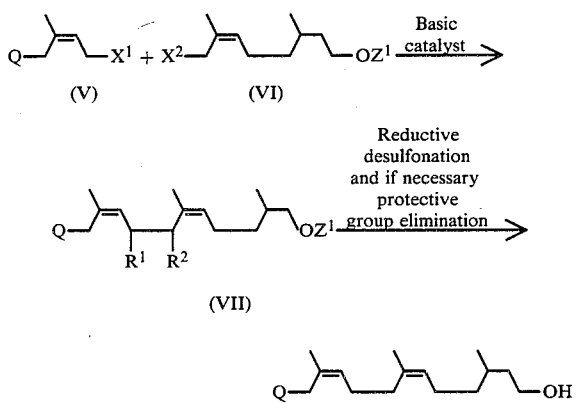

In the above schema, Q is as defined above, one of $X^1$ and $X^2$ is a halogen atom and the other is an arylsulfonyl group, $Z^1$ is a hydrogen atom or a hydroxyl-protecting group, one of $R^1$ and $R^2$ is a hydrogen atom and the other is an arylsulfonyl group provided that $R^1=H$ when $X^1$ is a halogen atom and $R^2=H$ when $X^2$ is a halogen atom.

The polyprenyl compounds and mixtures thereof obtainable by the method of the present invention are also useful, for instance as cosmetic bases or ointment bases or as the raw materials for the production thereof.

The following nonlimitative examples illustrate the invention in more detail. In the examples, the infrared (IR) analysis was always performed by the liquid film method, and the nuclear magnetic resonance (NMR) analysis was conducted in $CDCl_3$ with tetramethylsilane (TMS) as an internal standard. The field desorption mass spectrometry (FD-MASS) analysis data values are values corrected on the $^1H$, $^{12}C$, $^{16}O$ and $^{79}Br$ basis.

EXAMPLE 1

Leaves (10 kg; undried weight) of *Pinus densiflora as collected early December in Kurashiki City* were air-dried at about 50° C. for 24 hours and then immersed in 80 liters of chloroform at room temperature (about 10° C.) for 1 week for extraction. The chloroform was distilled off from the extract, 5 liters of hexane was added to the concentrate thus obtained, the insoluble matter was filtered off, and the filtrate was concentrated and subjected to silica gel chromatography using chloroform as the developing solvent. There was thus obtained about 6.4 g of a fraction showing an Rf value of 0.51 in thin layer chromatography [Merck thin layer chromatographic plate coated with silica gel $60F_{254}$ to a layer thickness of 0.25 mm; developing solvent: n-hexane-ethyl acetate=9:1 (by volume); developed 10 cm]. In the above thin layer chromatography, solanesyl acetate gave an Rf value of 0.40. To this oily fraction was added about 200 ml of acetone for dissolution of acetone-soluble components, the mixture was filtered, and the filtrate was concentrated. The thus-obtained oil was heated with 200 ml of methanol, 20 ml of water and 10 g of sodium hydroxide at 65° C. for 2 hours, then the methanol was distilled off, diethyl ether (200 ml) was added to the residue for extraction, the ether layer was washed five times with about 50 ml of saturated aqueous sodium chloride and then dried over anhydrous sodium sulfate, and the solvent was then distilled off to give 5.1 g of an oil. This oil was chromatographed over about 300 g of silica gel with a n-hexane-diisopropyl ether (90:10 by volume) mixture as the eluent to give 4.4 g of an oily fraction showing an Rf value of 0.19 in the above thin layer chromatography. This oily fraction was a polyprenol fraction having a purity of not less than 90%. The molecular weight distribution measured for this oily fraction is shown below. The data indicate the area proportions of individual peaks in the chromatogram obtained by high performance liquid chromatography using a Merck semipreparative high performance liquid chromatography column LiChrosorb RP 18-10 ($C_{18}$ type) with an acetone-methanol (90:10) mixture as the eluent and a differential refractometer as the detector.

| Peak No. | Value of $\underline{n}$ (Number of cis-isoprene units) | Area proportion (%) |
| --- | --- | --- |
| 1 | 10 | 2.4 |
| 2 | 11 | 3.0 |
| 3 | 12 | 9.9 |
| 4 | 13 | 32.2 |
| 5 | 14 | 34.3 |
| 6 | 15 | 11.5 |
| 7 | 16 | 2.5 |
| 8 | 17 | 2.2 |
| 9 | 18 | 1.6 |

The average number for n for the above polyprenol mixture was 13.6.

The individual components were separated from the above oily product by using the same high performance liquid chromatography as mentioned above. By mass spectrometry, infrared spectroscopy, $^1$H-NMR spec-troscopy and $^{13}$C-NMR spectroscopy, these components were identified as polyprenols having the structure represented by general formula (I) wherein A is a hydroxyl group.

The results of FD-MASS of these components and their δ values in $^1$H-NMR spectra are summarized in Table 2. The δ values of these components in $^{13}$C-NMR spectra are summarized in Table 3.

In the $^1$H-NMR data, (b) represents a broad signal; (d), a doublet signal; and (t), a triplet signal.

TABLE 2

| Value n (Number of cis-isoprene units) | FD-MASS (m/e) Found | FD-MASS (m/e) Calcd. | $^1$H—NMR δ (ppm) =CHCH$_2$OH | $^1$H—NMR δ (ppm) =CH— | $^1$H—NMR δ (ppm) —CH$_2$OH | $^1$H—NMR δ (ppm) —CH$_2$— |
|---|---|---|---|---|---|---|
| 10 | 902 | 902 | 5.44(t) | 5.13(b) | 4.08(d) | 2.04(b) |
| 11 | 970 | 970 | 5.44(t) | 5.13(b) | 4.08(d) | 2.04(b) |
| 12 | 1038 | 1038 | 5.44(t) | 5.12(b) | 4.08(d) | 2.04(b) |
| 13 | 1106 | 1106 | 5.43(t) | 5.12(b) | 4.08(d) | 2.04(b) |
| 14 | 1174 | 1174 | 5.44(t) | 5.12(b) | 4.08(d) | 2.04(b) |
| 15 | 1242 | 1242 | 5.44(t) | 5.13(b) | 4.08(d) | 2.04(b) |
| 16 | 1310 | 1310 | 5.44(t) | 5.14(b) | 4.08(d) | 2.04(b) |
| 17 | 1378 | 1378 | 5.44(t) | 5.13(b) | 4.08(d) | 2.04(b) |
| 18 | 1446 | 1446 | 5.43(t) | 5.13(b) | 4.08(d) | 2.05(b) |

| Value n (Number of cis-isoprene units) | $^1$H—NMR δ (ppm) H$_3$C, H / —CH$_2$, CH$_2$OH | $^1$H—NMR δ (ppm) H$_3$C, H / —CH$_2$, CH$_2$— | $^1$H—NMR δ (ppm) H$_3$C, CH$_2$— / —CH$_2$, H |
|---|---|---|---|
| 10 | 1.74 | 1.68 | 1.60 |
| 11 | 1.74 | 1.68 | 1.60 |
| 12 | 1.74 | 1.68 | 1.60 |
| 13 | 1.74 | 1.68 | 1.60 |
| 14 | 1.74 | 1.68 | 1.60 |
| 15 | 1.74 | 1.68 | 1.60 |
| 16 | 1.74 | 1.68 | 1.60 |
| 17 | 1.74 | 1.68 | 1.60 |
| 18 | 1.74 | 1.68 | 1.60 |

TABLE 3

| Value n (Number of cis-isoprene units) | $^{13}$C—NMR δ (ppm) \C= | =CH— | —CH$_2$OH | CH$_3$ / CH$_2$ | CH$_3$ / CH$_2$ | CH$_3$ / CH$_2$ | CH$_3$ / CH$_2$ | CH$_3$ / CH$_2$ |
|---|---|---|---|---|---|---|---|---|
| 10 | 135.17 | 125.09 | 59.00 | 39.78 | 32.27 | 32.05 |
| 11 | 135.17 | 125.09 | 59.00 | 39.77 | 32.27 | 32.04 |
| 12 | 135.17 | 125.10 | 58.99 | 39.78 | 32.28 | 32.05 |
| 13 | 135.16 | 125.08 | 58.99 | 39.78 | 32.27 | 32.05 |
| 14 | 135.17 | 125.09 | 59.00 | 39.77 | 32.27 | 32.04 |
| 15 | 135.15 | 125.12 | 58.99 | 39.78 | 32.29 | 32.05 |
| 16 | 135.15 | 125.11 | 58.98 | 39.77 | 32.28 | 32.05 |
| 17 | 135.15 | 125.12 | 59.00 | 39.77 | 32.29 | 32.05 |
| 18 | 135.16 | 125.10 | 58.98 | 39.77 | 32.29 | 32.05 |

| Value n (Number of cis-isoprene units) | —C—NMR δ (ppm) CH$_3$ / CH$_2$— | CH$_3$, H | CH$_3$ / CH$_3$ | CH$_3$ / CH$_3$, H | CH$_3$ / H |
|---|---|---|---|---|---|
| 10 | 26.47 | 23.42 | 25.67 | 17.65 | 15.98 |
| 11 | 26.47 | 23.42 | 25.67 | 17.64 | 15.98 |
| 12 | 26.47 | 23.42 | 25.66 | 17.64 | 15.98 |
| 13 | 26.48 | 23.42 | 25.67 | 17.65 | 15.99 |
| 14 | 26.47 | 23.42 | 25.66 | 17.64 | 15.97 |
| 15 | 26.49 | 23.42 | 25.65 | 17.65 | 15.99 |
| 16 | 26.49 | 23.42 | 25.65 | 17.64 | 15.98 |
| 17 | 26.49 | 23.41 | 25.66 | 17.65 | 15.99 |
| 18 | 26.48 | 23.41 | 25.64 | 17.64 | 15.99 |

EXAMPLE 2

Leaves of *Pinus thunbergii* (5 kg; undried weight) as collected in Kurashiki City early December were dried with hot air, then finely chopped in a mixer and extracted with 40 liters of a petroleum ether-acetone (4:1 by volume) mixture at room temperature (about 25° C.)

for 5 days. The extract was washed with water and dried over anhydrous sodium sulfate and then the solvent was distilled off to give a residue (about 100 g). To the residue was added 1 liter of n-hexane for dissolution of n-hexane-soluble components, the mixture was filtered, and the filtrate was concentrated and subjected to silica gel column chromatography with a n-hexane diethyl ether (95:5 by volume) mixture as the eluent to give about 2.7 g of an oily fraction showing Rf values of 0.50 and 0.19 in the same thin layer chromatography as used in Example 1. To the oily substance was added about 50 ml of acetone for dissolution of acetone-soluble components, the mixture was filtered and the filtrate was chromatographed on about 100 g of silica gel with a n-hexane-diethyl ether (95:5 by volume) mixture as the eluent to give 2.2 g of an oil. This oil was a polyprenyl acetate fraction having a purity of not less than 90% and the molecular weight distribution measured for this oil was as shown below. The molecular weight distribution was determined based on the area proportions of individual peaks in the chromatogram obtained by high performance liquid chromatography using a Waters high preformance liquid chromatography column $\mu$ Bondapack/$C^{18}$ with an acetone-methanol (70:30 by volume) mixture as the eluent and a differential refractometer as the detector.

| Peak No. | Value of n (Number of cis-isoprene units) | Area proportion (%) |
|---|---|---|
| 1 | 10 | 1.7 |
| 2 | 11 | 2.7 |
| 3 | 12 | 10.8 |
| 4 | 13 | 32.5 |
| 5 | 14 | 32.5 |
| 6 | 15 | 12.6 |
| 7 | 16 | 4.4 |
| 8 | 17 | 2.0 |
| 9 | 18 | 0.8 |

The mean value for n for the polyprenyl acetate mixture thus obtained was 13.5.

Each component was isolated from the above oily fraction (having a polyprenyl acetate content of not less than 90%) by the same high performance liquid chromatography as in Example 1 and identified as a polyprenyl acetate of general formula (I) wherein A is an acetoxy group by mass spectrometry, infrared spectroscopy, $^1$H-NMR spectroscopy and $^{13}$C-NMR spectroscopy. The results of FD-MASS analysis for the respective components are shown in Table 4.

TABLE 4

| Value of n (Number of cis-isoprene units) | FD-MASS (m/e) | |
|---|---|---|
| | Found | Calculated |
| 10 | 944 | 944 |
| 11 | 1012 | 1012 |
| 12 | 1080 | 1080 |
| 13 | 1148 | 1148 |
| 14 | 1216 | 1216 |
| 15 | 1284 | 1284 |
| 16 | 1352 | 1352 |
| 17 | 1420 | 1420 |
| 18 | 1488 | 1488 |

The polyprenols obtained by hydrolyzing the respective components by the same hydrolysis reaction as performed in Example 1 gave quite the same $^1$H-NMR spectra, $^{13}$C-NMR spectra and infrared absorption spectra as those obtained for the corresponding polyprenols identical in the value of n as obtained in Example 1.

EXAMPLES 3–23

Leaves of Pinus densiflora as collected in Kurashiki City late October were air dried at about 60° C. for 65 hours, and divided into 100-g portions. Each portion was immersed in 1 liter of the solvent indicated in Table 5, and the extraction was effected at room temperature (about 20° C.) for 7 days. The extracting solvent was distilled off from the extract, and the residue was weighed. The weight thus found is shown in Table 5 in the "total weight of extract" column. The extract (residue) was dissolved in 200 ml of hexane, the solution was washed three times with about 100 ml of a methanol-water (9:1 by volume) mixture and dried over anhydrous magnesium sulfate, and then the solvent was distilled off to give an oil. The oil was heated with 50 ml of methanol and 1 g of potassium hydroxide at 65° C. for 2 hours, then the methanol was distilled off, diethyl ether (100 ml) was added to the residue for extraction, the ether layer was washed three times with about 50 ml of saturated aqueous sodium chloride and dried over anhydrous magnesium sulfate, and then the solvent was distilled off to give an oil. This oil was chromatographed on 100 g of silica gel with a n-hexane-ethyl acetate (9:1 by volume) mixture to give a fraction (polyprenol mixture) showing an Rf value of 0.19 in the same thin layer chromatography as in Example 1. The weight of this fraction is shown in Table 5 in the "polyprenol content" column. The composition of each polyprenol mixture thus obtained was in substantial agreement with that of the polyprenol mixture obtained in Example 1 irrespective of the solvent species used.

TABLE 5

| Ex. No. | Solvent | Total weight of extract (g) | Polyprenol content (g) |
|---|---|---|---|
| 3 | n-Hexane | 4.42 | 0.48 |
| 4 | Petroleum ether | 4.53 | 0.50 |
| 5 | Benzene | 6.21 | 0.51 |
| 6 | Chloroform | 7.92 | 0.43 |
| 7 | Carbon tetrachloride | 5.38 | 0.42 |
| 8 | Diethyl ether | 7.25 | 0.52 |
| 9 | Tetrahydrofuran | 10.05 | 0.42 |
| 10 | Methanol | 15.28 | 0.14 |
| 11 | Ethanol | 12.38 | 0.25 |
| 12 | Isopropyl alcohol | 6.21 | 0.32 |
| 13 | Acetone | 9.21 | 0.53 |
| 14 | Ethyl acetate | 7.62 | 0.51 |
| 15 | Acetone-hexane (20:80 by vol.) | 5.98 | 0.51 |
| 16 | Acetone-hexane (50:50 by vol.) | 8.01 | 0.57 |
| 17 | Acetone-chloroform (20:80 by vol.) | 8.65 | 0.47 |
| 18 | Acetone-chloroform (50:50 by vol.) | 7.59 | 0.52 |
| 19 | Methanol-chloroform (20:80 by vol.) | 16.21 | 0.51 |
| 20 | Methanol-chloroform (50:50 by vol.) | 18.31 | 0.45 |
| 21 | Diethyl ether-hexane (20:80 by vol.) | 5.92 | 0.47 |
| 22 | Methanol-acetone (20:80 by vol.) | 11.32 | 0.50 |
| 23 | Methanol-acetone (50:50 by vol.) | 15.02 | 0.37 |

EXAMPLE 24

Leaves of Pinus sylvestris (600 g; undried weight) as collected in Kyoto City late December were air-dried at about 57° C. for 62 hours and then immersed in 7 liters of an acetone-hexane (1:4 by volume) mixture at room temperature (about 10° C.) for a week for extraction. The solvent was then distilled off from the extract, 200 ml of hexane was added to the concentrate, the insoluble matter was filtered off, and the filtrate was concentrated and subjected to silica gel column chromatography using a hexanediethyl ether (19:1 by volume) mixture as the developing solvent to give about 1.1 g of an oil as a fraction showing an Rf value of 0.51 in the same thin layer chromatography as used in Example 1. Then acetone (about 20 ml) was added to the above oil for dissolution of acetone-soluble components, the mixture was filtered, and the filterate was concentrated to give an oil. This oil was a polyprenyl acetate fraction having a purity of not less than 90% and the molecular weight distribution measured therefor in the same manner as in Example 2 was as shown below.

| Peak No. | Value of n (Number of cis-isoprene units) | Area proportion (%) |
| --- | --- | --- |
| 1 | 10 | 3.0 |
| 2 | 11 | 8.0 |
| 3 | 12 | 24.7 |
| 4 | 13 | 35.8 |
| 5 | 14 | 19.2 |
| 6 | 15 | 6.5 |
| 7 | 16 | 2.8 |

The mean value for n for the thus-obtained polyprenyl acetate mixture was 12.9.

Each component was isolated from the above oil (having a polyprenyl acetate content of not less than 90%) by the same high performance liquid chromatography as used in Example 1 and identified as a polyprenyl acetate of general formula (I) wherein A is an acetoxy group by mass spectrometry, infrared spectroscopy, $^1$H-NMR spectroscopy and $^{13}$C-NMR spectroscopy.

EXAMPLE 25

Leaves of *Pinus strobus* (3.2 kg; undried weight) as collected in Kyoto City late December were air-dried at about 60° C. for 61 hours and then immersed in 45 liters of an acetone-hexane (1:4 by volume) mixture at room temperature (about 10° C.) for a week for extraction. The solvent was distilled off from the extract and, to the concentrate thus obtained, there was added 1.2 liters of hexane. The insoluble matter was filtered off, and the filtrate was concentrated and then chromatographed on a silica gel column using a hexane-diethyl ether (19:1 by volume) mixture as the developing solvent to give about 3.6 g of an oil as a fraction showing an Rf value of 0.51 in the same thin layer chromatography as used in Example 1. Acetone (about 70 ml) was added to the above oil for dissolution of acetone-soluble components, the mixture was filtered, and the filtrate was concentrated to give an oil. This oil was a polyprenyl acetate fraction having a purity of not less than 90%. The molecular weight distribution measured for this oil in the same manner as in Example 2 was as shown below.

| Peak No. | Value of n (Number of cis-isoprene units) | Area proportion (%) |
| --- | --- | --- |
| 1 | 11 | 1.8 |
| 2 | 12 | 6.4 |
| 3 | 13 | 21.5 |
| 4 | 14 | 38.8 |
| 5 | 15 | 22.3 |
| 6 | 16 | 6.7 |
| 7 | 17 | 1.8 |
| 8 | 18 | 0.9 |

The mean value for n for the polyprenyl acetate mixture obtained here was 14.0.

Each component was isolated from the above oil (having a polyprenyl acetate content of not less than 90%) by the same high performance liquid chromatography as in Example 1 and identified as a polyprenyl acetate of formula (I) wherein A is an acetoxy group by mass spectrometry, infrared spectroscopy, $^1$H-NMR spectroscopy and $^{13}$C-NMR spectroscopy.

EXAMPLE 26

To a solution of 1.24 g of the polyprenol of general formula (I) wherein n=15 and A=OH as obtained from the leaves of *Pinus densiflora* in the same manner as in Example 1 and 1.0 g of pyridine in dry diethyl ether, there was added dropwise 1.2 g of acetic anhydride at room temperature. After completion of the dropping, the mixture was stirred at room temperature overnight. The reaction mixture was washed with saturated aqueous sodium chloride and dried over anhydrous magnesium sulfate, and then the diethyl ether was distilled off. The remaining light-yellow viscous oil was purified by silica gel column chromatography (developing solvent: hexane-ethyl acetate) to give 1.05 g of a pale yellow oil. Infrared spectroscopic analysis revealed that the absorption at about 3,300 cm$^{-1}$ due to the OH group in the starting polyprenol has disappeared with appearance of the absorptions at 1,745 cm$^{-1}$ and 1,255 cm$^{-1}$ due to —OCOCH$_3$. In NMR spectroscopy, the signal (doublet, $\delta=4.08$) assignable to —$\underline{CH_2}$OH in the starting polyprenol was no more observed and a new signal (doublet, $\delta=4.55$) assignable to —$\underline{CH_2}$OCOCH$_3$ was observed. The signal assignable to —$\underline{CH_2}$OCOCH$_3$ was observed overlapping with the signal ($\delta=2.04$) assignable to —CH$_2$—C=. FD-MASS analysis gave m/e=1,284. These facts identified the product as the polyprenyl acetate of general formula (I) wherein n=15 and A=OCOCH$_3$. Polyprenyl acetates in which n is other than 15 and polyprenyl acetate mixtures with n being distributed within the range of 10–18 in any desired patterns could also be synthesized by the same procedure.

EXAMPLE 27

The polyprenol of general formula (I) wherein n=14 and A=OH (1.17 g) as obtained from *Pinus densiflora* leaves in the same manner as in Example 1, 0.5 g of methyl oleate and 0.01 g of sodium hydride were dissolved in 50 ml of toluene, and the solution was heated at 110° C. in a nitrogen atmosphere for 24 hours. The reaction mixture was cooled to room temperature, washed with saturated aqueous sodium chloride and dried over anhydrous magnesium sulfate, and the solvent was then distilled off to give a yellow liquid. This was purified by silica gel column chromatography (developing solvent: hexane-ethyl acetate) to give 0.44 g of a colorless, viscous liquid. IR analysis of this liquid revealed the disappearance of the absorption at about 3,300 cm$^{-1}$ due to the OH group of the starting polyprenol. FD-MASS analysis gave the value m/e=1,438. These facts identified this product as the polyprenyl oleate of general formula (I) wherein n=14 and A=O-COC$_{17}$H$_{33}$. Polyprenyl oleate species in which n is other than 14 and polyprenyl oleate mixtures with n being distributed within the range of 10–18 in any desired patterns could also be synthesized by the same procedure.

EXAMPLE 28

To a mixture of 1.11 g of the polyprenol of general formula (I) wherein n=13 and A=OH as obtained from *Pinus thunbergii* leaves in the same manner as in Example 1 and 10 ml of pyridine, there was added 0.28 g of benzoyl chloride at room temperature, and the mixture was stirred at room temperature overnight. Then, the reaction mixture was poured into about 150 ml of water and extracted with diethyl ether, the ether layer was washed in sequence with saturated aqueous sodium chloride, diluted hydrochloric acid, saturated aqueous sodium hydrogen carbonate and saturated aqueous sodium chloride, and dried over magnesium sulfate, and the diethyl ether was then distilled off. The remaining yellow liquid was purified by silica gel column chromatography (developing solvent: hexane-ethyl acetate) to give 0.79 g of a light-yellow liquid. IR analysis of this liquid revealed the disappearance of the absorption due to the OH group of the starting polyprenol and appearance of the absorptions at 1,715 cm$^{-1}$ and 1,270 cm$^{-1}$ due to the ester group. FD-MASS analysis gave m/e=1,210. These facts identified this liquid as the polyprenyl benzoate of general formula (I) wherein n=13 and A=OCOC$_6$H$_5$. Polyprenyl benzoate species in which n is other than 13 and polyprenyl benzoate mixtures with n being distributed in the range of 10–18 in any desired patterns could also be synthesized by the same procedure.

REFERENCE EXAMPLE 1

In a three-necked flask purged with argon, there were placed 0.316 g (13 mmol) of magnesium chips, 0.5 ml of anhydrous tetrahydrofuran and 0.08 ml of 1,2-dibromoethane, and the mixture was heated by means of a drier until violent foaming occurred. Then, a solution of 2.51 g (10 mmol) of 2-(4-bromo-3-methylbutoxy)tetrahydro-2H-pyran in 3.0 ml of anhydrous tetrahydrofuran was added dropwise to the activated magnesium at a rate such that the solvent could just keep boiling. After completion of the dropping, the mixture was stirred at 70° C. for 15 minutes. Thereto was added 60 ml of anhydrous tetrahydrofuran to give a Grignard reagent solution.

Separately, a solution of 6.42 g (5 mmol) of the polyprenyl acetate of general formula (I) wherein n=15 and A=—OCOCH$_3$ in 15 ml of anhydrous tetrahydrofuran and 2.0 ml of a 0.1M solution of Li$_2$CuCl$_4$ in anhydrous tetrahydrofuran were placed in a three-necked flask purged with argon. Thereto was added dropwise the Grignard reagent solution preliminarily prepared at 0° C. over 1 hour with stirring. Thereafter, the stirring was continued at 0° C. for 2 hours. Then, saturated aqueous ammonium chloride was added to the reaction mixture for hydrolysis, and the whole mixture was extracted with ether. The ether layer was washed with saturated aqueous sodium chloride and dried over anhydrous magnesium sulfate, and the solvent was distilled off using a rotary evaporator to give 7.78 g of a light-yellow liquid. In silica gel thin layer chromatography (developing solvent: hexane-ethyl acetate=97:3), this liquid showed a main spot at Rf=0.35. In FD-MASS analysis of this light-yellow liquid, the signal m/e=1,284 showing the presence of the starting polyprenyl acetate was not detected at all, but the signal m/e=1,396 was detected as a main peak, identifying it as the compound of general formula (III) wherein n=15 and Z=tetrahydro-2H-pyranyl group.

The light-yellow liquid was dissolved in 40 ml of hexane, and 0.13 g (0.5 mmol) of p-toluenesulfonic acid-pyridine and 20 ml of ethanol were added. The solution was heated at 55° C. with stirring for 3 hours. After cooling, 0.21 g of sodium carbonate was added for neutralization, and the solvent was distilled off using a rotary evaporator. The concentrate thus obtained was dissolved in ether, and the solution was washed with saturated aqueous sodium hydrogen carbonate and then with saturated aqueous sodium chloride, and dried over anhydrous magnesium sulfate. The solvent was removed using a rotary evaporator, and the remaining oily substance was heated at 150° C. at 0.5 Torr for 30 minutes to remove low-boiling components. The residual liquid was purified by silica gel column chromatography (developing solvent: hexane-ethyl acetate=9:1) to give 5.47 g of a colorless and clear liquid. This gave a single spot (Rf=0.19) in silica gel thin layer chromatography (developing solvent: hexane-ethyl acetate=9:1). The analytical results shown below identified this liquid as the compound of general formula (A) wherein j=15.

FD-MASS analysis: m/e=1,312 (calculated value: 1,312).

IR analysis (cm$^{-1}$): 830, 1060, 1376, 1440, 2850, 2920, 3320

$^{13}$C-NMR analysis (ppm/intensity): 135.365/430, 135.229/3567, 135.005/349, 134.937/290, 131.210/213, 125.071/5242, 124.993/499, 124.448/505, 124.282/463, 124.214/445, 61.241/551, 40.029/541, 39.757/683, 37.548/582, 32.245/5500, 32.021/456, 29.316/528, 26.825/492, 26.699/548, 26.436/5166, 25.677/542, 25.308/567, 23.430/6330, 19.557/548, 17.679/353, 16.006/640

$^1$H-NMR analysis (ppm, shape of signal, proton ratio): 5.10(b, 18H), 3.66(m, 2H), 2.03(b, 70H), 1.68(s, 48H), 1.60(s, 9H), 1.80–1.10(m, 5H), 0.91(d, 3H)

REFERENCE EXAMPLE 2

12.4 g of the polyprenol of general formula (I) in which A=OH and n=15 and 1 ml of pyridine were added to 200 ml of n-hexane. To the resulting solution was added dropwise 2.0 g of phosphorus tribromide in an atmosphere of nitrogen. After the addition, the mixture was stirred overnight at room temperature in an atmosphere of nitrogen. The n-hexane solution was transferred to a separating funnel, washed ten times with about 50 ml of water and then dried over anhydrous magnesium sulfate. The n-hexane was distilled off to give 12.0 g of a slightly yellow liquid product. NMR spectroscopy of this product revealed that the signal (doublet, δ=4.08) assignable to the —CH$_2$OH group of the starting polyprenol had disappeared and a signal (doublet, δ=3.91) assignable to —CH$_2$Br had newly appeared. FD MASS analysis of this liquid product gave m/e=1304. Based on these analytical data, the above product was identified to be the polyprenyl bromide of formula (II) in which X=Br and Q is the group of formula (IV) where n=15.

The polyprenyl bromide (12.0 g) was dissolved in a mixture of 100 ml of N,N-dimethylformamide and 100 ml of tetrahydrofuran, and 3.1 g of sodium phenylsulfinate was added. The mixture was stirred at room temperature for 17 hours and then at 50° C. for 1 hour. The solvent was removed using a rotary evaporator, and water was added to the reaction mixture, followed by extraction with benzene. The benzene layer was washed with water and dried over anhydrous magnesium sulfate. Removal of the solvent gave a yellow liquid. The liquid was purified by silica gel column chromatography using hexane-ethyl acetate as the eluent to give 8.7 g of a pale yellow liquid. $^1$H-NMR analysis of this liquid demonstrated that the signal (doublet, $\delta=3.91$) assignable to —CH$_2$Br of the starting polyprenyl bromide had disappeared and a signal (doublet, $\delta=3.77$) assignable to —C$\underline{H}_2$SO$_2$C$_6$H$_5$ and a signal (multiplet, $\delta=7.31-7.93$) assignable to —SO$_2$C$_6$$\underline{H}_5$ had newly appeared. FD-MASS analysis of the liquid gave m/e=1366. From these analytical data, this liquid was identified to be a polyprenyl phenyl sulfone of formula (V) in which $X^1=$—SO$_2$C$_6$H$_5$ and Q is the group of formula (IV) where n=15. This polyprenyl sulfone (6.83 g) was dissolved in a mixture of 30 ml of anhydrous tetrahydrofuran and 3 ml of anhydrous hexamethylphosphoramide, the solution was cooled to about $-10°$ to $0°$ C., 3.28 ml of a 1.6M solution of n-butyllithium in hexane was added under nitrogen gas, the mixture was stirred for 15 minutes, and then a solution of 1.92 g of 8-bromo-3,7-dimethyl-6Z-octenyl tetrahydropyranyl ether in 2 ml of anhydrous tetrahydrofuran was added dropwise. After completion of the dropping, the mixture was stirred at the same temperature for an hour and then at room temperature (about 20° C.) overnight. The reaction mixture was poured into 200 ml of water and extracted with methylene chloride. The methylene chloride layer was washed with water and dried over anhydrous magnesium sulfate, and then the solvent was distilled off under reduced pressure to give a light-yellow liquid. This liquid was purified by silica gel column chromatography (developing solvent: methylene chloride-ethyl acetate) to give 6.74 g of a pale yellow liquid. Based on the analytical results shown below, this liquid was identified as the compound of general formula (VII) wherein Q is the group of formula (IV) in which n=15, $R^1=$—SO$_2$C$_6$H$_5$, $R^2=$H and

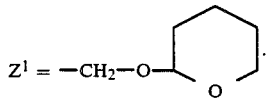

FD-MASS: m/e=1604
IR(cm$^{-1}$): 1660, 1590, 1450, 1380, 1310, 1145, 1120, 1080, 1035, 1020, 835
$^1$H-NMR($\delta_{ppm}^{CDC3}$): 7.31–7.95(m, 5H, —SO$_2$C$_6$$\underline{H}_5$), 4.75–5.35(bs 19H,

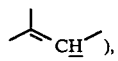

4.46(br, 1H,

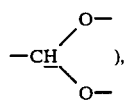

3.10–4.00(m, 5H)

Being a macromolecule, this compound gave a complicated $^1$H-NMR spectrum. Therefore, the above signals were used for the structural analysis.

This compound (6.72 g) was dissolved in 200 ml of ethanol. Thereto was added 30 ml of 1N hydrochloric acid, and the mixture was stirred at room temperature for 4 hours. The reaction mixture was neutralized with aqueous sodium hydrogen carbonate, most of the ethanol was distilled off under reduced pressure, the residue was poured into 200 ml of water, and the mixture was extracted with hexane. The hexane layer was washed with water and dried over anhydrous magnesium sulfate, the hexane was distilled off, and the residue was purified by silica gel column chromatography (developing solvent: methylene chloride-ethyl acetate) to give 6.08 g of a colorless to slightly yellow liquid. Based on the analytical results shown below, this product was identified as the compound of the formula

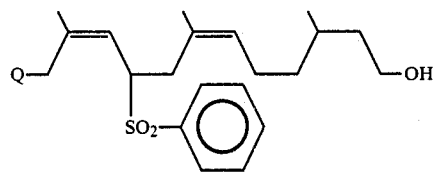

wherein Q is the group of formula (IV) in which n=15.
FD-MASS: m/e=1520
IR(cm$^{-1}$): ~3500, 1670, 1590, 1440, 1375, 1290, 1140, 1090, 1070, 1050, 830
$^1$H-NMR($\delta_{ppm}$ $^{CDCl3}$): 7.31–7.90(m, 5H, SO$_2$C$_6$$\underline{H}_5$) 4.75–5.35(br, 19H,

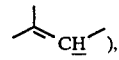

3.36–4.05(m, 3H, >C$\underline{H}$—SO$_2$C$_6$H$_5$+—C$\underline{H}_2$OH)

The above compound (5.30 g) was dissolved in 10 of anhydrous ethylamine, and the solution was cooled to $-20°$ C. Thereto was added 0.50 g of metallic lithium in a nitrogen atmosphere, and the mixture was stirred. After the reaction mixture turned blue, the stirring was further continued for 15 minutes. Then, 2 ml of isoprene and 2 ml of methanol were added, followed by 2 g of ammonium chloride for decomposing the excess lithium. After the system turned white, the mixture was poured into 200 ml of water and extracted with hexane. The hexane layer was washed with water and dried over anhydrous magnesium sulfate, and the hexane was then distilled off under reduced pressure. The residue thus obtained was purified by silica gel column chromatography (developing solvent: methylene chloride-ethyl acetate) to give 3.51 g of a colorless, viscous liquid. The results of FD-MASS, IR and $^{13}$C-NMR analyses of this liquid were in good agreement with those for the final product of Reference Example 1 and the liquid was thus identified as the compound of general formula (A) wherein J=15.

What is claimed is:
1. A method of preparing a polyprenyl compound or a mixture of polyprenyl compounds, represented by the general formula:

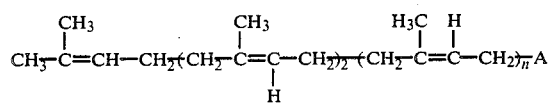  (I)

wherein A is a hydroxyl or acyloxy group,

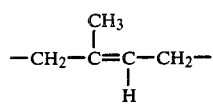

represents a trans-isoprene unit,

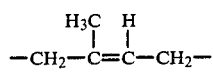

represents a cis isoprene unit and n is an integer of 10 to 18, which comprises
  extracting the leaves of a plant belonging to the genus Pinus L. of the family Pinaceae with an organic solvent to obtain an extract,
  separating the extract into fractions by fractional dissolution and chromatography, and
  confirming formation of a fraction containing polyprenyl compounds by determining Rf values of said fractions by thin layer chromatography, on a plate for thin layer chromatography coated with silica gel and a mixture of n-hexane and ethyl acetate in a volume ratio of 9:1 as a developing solvent (developed 10 cm) under the conditions such that solanesyl acetate as a standard substance gives an Rf value of 0.40–0.45, with an Rf value of 0.18–0.25 in thin layer chromatography confirming formation of a fraction essentially consisting of polyprenyl compounds of formula (I) wherein A is a hydroxyl group and with an Rf value of 0.50–0.55 in thin layer chromatography confirming formation of a fraction essentially consisting of polyprenyl compounds of general formula (I) wherein A is an acetoxy group.

2. The method of claim 1, wherein the chromatography step for separating the extract into fractions is followed by at least one step of chromatography, fractional dissolution, fractional refrigerating precipitation and molecular distillation.

3. The method of claim 1, wherein the organic solvent is selected from the group consisting of hydrocarbons, halogenated hydrocarbons, ethers, esters and ketones.

4. The method of claim 1, wherein the extract is subjected to at least one reaction selected from among hydrolysis, esterification and transesterification.

5. The method of claim 1, wherein the isolated polyprenyl compound or mixture of polyprenyl compounds is subjected to at least one reaction selected from among hydrolysis, esterification and transesterification.

6. The method of claim 1, wherein the polyprenyl fraction contains substantial amounts of compounds of general formula (I) wherein n is 12, 13, 14, and 15, respectively, the total content of these compounds amounting to at least 70 percent by weight based on said polyprenyl fraction.

* * * * *